(12) United States Patent
Haines

(10) Patent No.: US 6,612,151 B2
(45) Date of Patent: Sep. 2, 2003

(54) DEVICE AND METHOD FOR DETERMINING FRICTION

(75) Inventor: Robert Christoper Haines, Huddersfield (GB)

(73) Assignee: ITF Licensing (UK) LTD, London (GB)

( * ) Notice: Subject to any disclaimer, the term of this patent is extended or adjusted under 35 U.S.C. 154(b) by 213 days.

(21) Appl. No.: 09/775,673

(22) Filed: Feb. 5, 2001

(65) Prior Publication Data

US 2001/0047679 A1 Dec. 6, 2001

(30) Foreign Application Priority Data

Feb. 3, 2000 (GB) .............................................. 0002520

(51) Int. Cl.[7] .............................................. G01N 19/02
(52) U.S. Cl. ............................................................ 73/9
(58) Field of Search ................................................ 73/9

(56) References Cited

U.S. PATENT DOCUMENTS 3,205,698 A * 9/1965 Shaw ............................... 73/9
5,195,357 A    3/1993 Takino et al.
6,016,685 A * 1/2000 Ekstrom et al. ................. 73/9

* cited by examiner

Primary Examiner—Robert Raevis
(74) Attorney, Agent, or Firm—Browdy and Neimark, P.L.L.C.

(57) ABSTRACT

The device consists of a rigid pendulum (1) pivoted at its upper end (2) and upon which a ball (5) is retained at its lower end in a holder (6), so that the center of the ball lies on or close to the longitudinal axis of the pendulum. The holder itself is attached to a shoe (3) which pivots about a point (4) on a projection offset from the bottom end of the pendulum, such that the shoe moves in an arc which lies in a vertical plane perpendicular to the vertical plane in which the pendulum swings. Movement of the shoe about this pivot allows the ball holder (6) and thus the ball (5) to move in an approximately radial direction with respect to the pendulum pivot (that is, along the axis of the pendulum when the ball center is on that axis) and the degree of movement of the shoe about its pivot is limited by stops (7a, 7b) provided on the pendulum. The complete pendulum device is supported in a tripod framework or alternative rigid support.

12 Claims, 3 Drawing Sheets

DEVICE AND METHOD FOR DETERMINING FRICTION

BACKGROUND OF THE INVENTION

1. Field of the Invention

The present invention relates to a device and a method for determining frictional force, more particularly the frictional force (coefficient of friction) between a games ball and a playing surface.

2. Description of the Related Art

Many games require that a ball be propelled by a player to rebound off a surface, as in for example tennis, golf, squash, cricket and so on. Generally, balls for such games are made to rigid technical specifications but surfaces often vary widely in composition and consistency and so the rebound of a ball may vary considerably in terms of its speed and angle. This can introduce significant and often undesirable playing characteristics into such games.

Complex electronic equipment is available for measuring the rebound performance of balls off surfaces consisting of 'black boxes' through which a ball is made to pass before and after obliquely striking a surface. However, such equipment is expensive, and because it is not readily portable and requires mains electricity, it does not lend itself to outdoor use. There is therefore a requirement for a simpler, less expensive measuring device which is portable and easy to use.

In considering the basis for such measurement it is convenient to consider the way in which the ball interacts with a surface by resolving its motion in two mutually perpendicular directions (ie perpendicular and parallel to the surface respectively) and to consider these two components separately. Measurement of the parameters of each component can then be used together to assess the mode of ball rebound from an oblique impact with the surface.

A simple test is available for assessing rebound performance perpendicular to the surface. This consists of measuring the percentage vertical rebound on dropping a ball from a fixed height onto that surface. No such simple test is available for assessing performance parallel to the surface, which requires measurement of the friction generated between the ball and surface during the time they are in contact.

SUMMARY OF THE INVENTION

It is an object of this invention to provide a device and a method for determining the coefficient of friction between a games ball and a playing surface.

The object described above is achieved by a device comprising:

- a rigid pendulum having first and second ends, mounted by a pivot at its first end to a frame placed on the surface, allowing the pendulum to describe a vertical arc over the surface;
- holding means for holding a ball adjacent the second end of the pendulum so as to permit controlled movement of the ball with respect to the pendulum;
- adjusting means for adjusting the position of the pivot relative to the surface, to ensure contact of the ball with the surface over a desired length of a lower portion of the arc; and
- measuring means for measuring the extent of the arc described by the pendulum following contact of the ball with the surface, so as to allow determination of the coefficient of friction between the ball and the surface.

The object described above is also achieved by the device mentioned above, in which the holding means comprises a holder which is attached to the pendulum by a rotatable shoe arranged such that the plane of the rotation of the shoe relative to the pendulum is perpendicular to the plane of the pendulum arc, and such that the center of the ball can move in a controlled manner in an approximately radial direction with respect to the pendulum pivot, and at a point where the pendulum is vertical, the center of the ball lies on a vertical line passing through that pivot.

The object described above is also achieved by the device mentioned above, wherein the shoe is provided with adjustable stops which control within fixed limits the extent of movement of the ball holder in said radial direction in order to control the length of contact between the ball and the surface.

The object described above is also achieved by the device mentioned above, wherein the shoe is pivoted from a lateral projection of the pendulum, allowing the holder and ball to be disposed underneath the end of the pendulum and thus allowing the ball to move substantially along the axis of the pendulum.

The object described above is also achieved by the device mentioned above, wherein a load is applied to the shoe by means of interchangeable springs so that the force applied by the ball to the surface in a direction normal to the surface may be varied. For example, a tension spring is extended between a point on the shoe and a point part-way along the pendulum.

To determine "sliding" friction between the ball and test surface, the ball is firmly fixed in the holder so that it cannot rotate under the frictional forces generated. Alternatively, the ball is mounted in the holder in such a way as to permit either free or restrained rotation of the ball within the holder, to allow determination of "rolling" friction.

The object described above is also achieved by the device mentioned above, wherein the adjusting means comprises a screw device mounted in the frame at a desired position thereon, thereby allowing adjustment of the height of the pendulum pivot above the surface.

The object described above is also achieved by the device mentioned above, wherein the adjusting means further comprises means for adjusting the position of the ball relative to the pendulum pivot.

The object described above is also achieved by the device mentioned above, wherein the measuring means comprises a scale placed parallel to the plane of the pendulum arc, and a pointer which is rotatable about the pendulum pivot to follow the swing of the pendulum; the pointer is equipped with a holding device, to hold it in position when the pendulum arc reaches its maximum extent following contact of the ball with the surface.

The device of the present invention can be applied to balls and surfaces used in the games of tennis, cricket, hockey and squash rackets among others.

The object described above is also achieved by a method of determining the frictional force between a games ball and a playing surface, comprising the steps of:

- retaining a rigid pendulum at one end to a pivot fixed above the surface, allowing the pendulum to swing vertically over the surface;
- mounting a ball adjacent the other end of the pendulum so as to permit limited movement of the ball with respect to the pendulum;
- adjusting the height of the pivot above the surface, in order to ensure contact of the ball with the surface over a desired length of the lower part of the pendulum swing;

measuring the extent of the pendulum swing following contact of the ball with the surface; and determining the frictional force between the ball and the surface based on the measured extent of the pendulum swing.

The object described above is also achieved by the method mentioned above, wherein;

in said mounting step, the ball is inserted in a holder attached to a rigid pendulum by a pivoted shoe;

in said adjusting step:

(i) the height of the pendulum pivot above the test surface is adjusted so that the moment of weight of the shoe, holder and ball only is applied to the surface through the ball and a fixed distance is set between the shoe and a fixed upper stop;

(ii) a spring is then fitted to apply a load to the shoe such that it is pressed down against a lower stop when the pendulum is not vertical and such that when the pendulum is vertical the spring becomes extended so that an additional force is applied to the surface through the ball; and (iii) the lower stop is adjusted to give a ball/surface contact path of known length as the pendulum describes its lower arc; and in said measuring step, the pendulum is raised to a pre-determined height and released so that the ball descends towards, then contacts and slides along the surface as the pendulum describes its arc, and the maximum angle of the pendulum's swing after contact has been made with the surface is measured by the slave pointer.

BRIEF DESCRIPTION OF THE DRAWINGS

The invention will now be described, by way of example with reference to the accompanying drawings in which.

DESCRIPTION OF THE PREFERRED EMBODIMENT

The device essentially consists of a rigid pendulum pivoted at its upper end and upon which a ball is retained at its lower end in a holder, so that the center of the ball lies on or close to the longitudinal axis of the pendulum. The holder itself is attached to a shoe which pivots about a point on a projection offset from the bottom end of the pendulum, such that the shoe moves in an arc which lies in a vertical plane perpendicular to the vertical plane in which the pendulum swings. Movement of the shoe about this pivot allows the ball holder and thus the ball to move in an approximately radial direction with respect to the pendulum pivot (that is, along the axis of the pendulum when the ball center is on that axis) and the degree of movement of the shoe about its pivot is limited by stops provided on the pendulum. The complete pendulum device is supported in a tripod framework or alternative rigid support.

Figure 1:
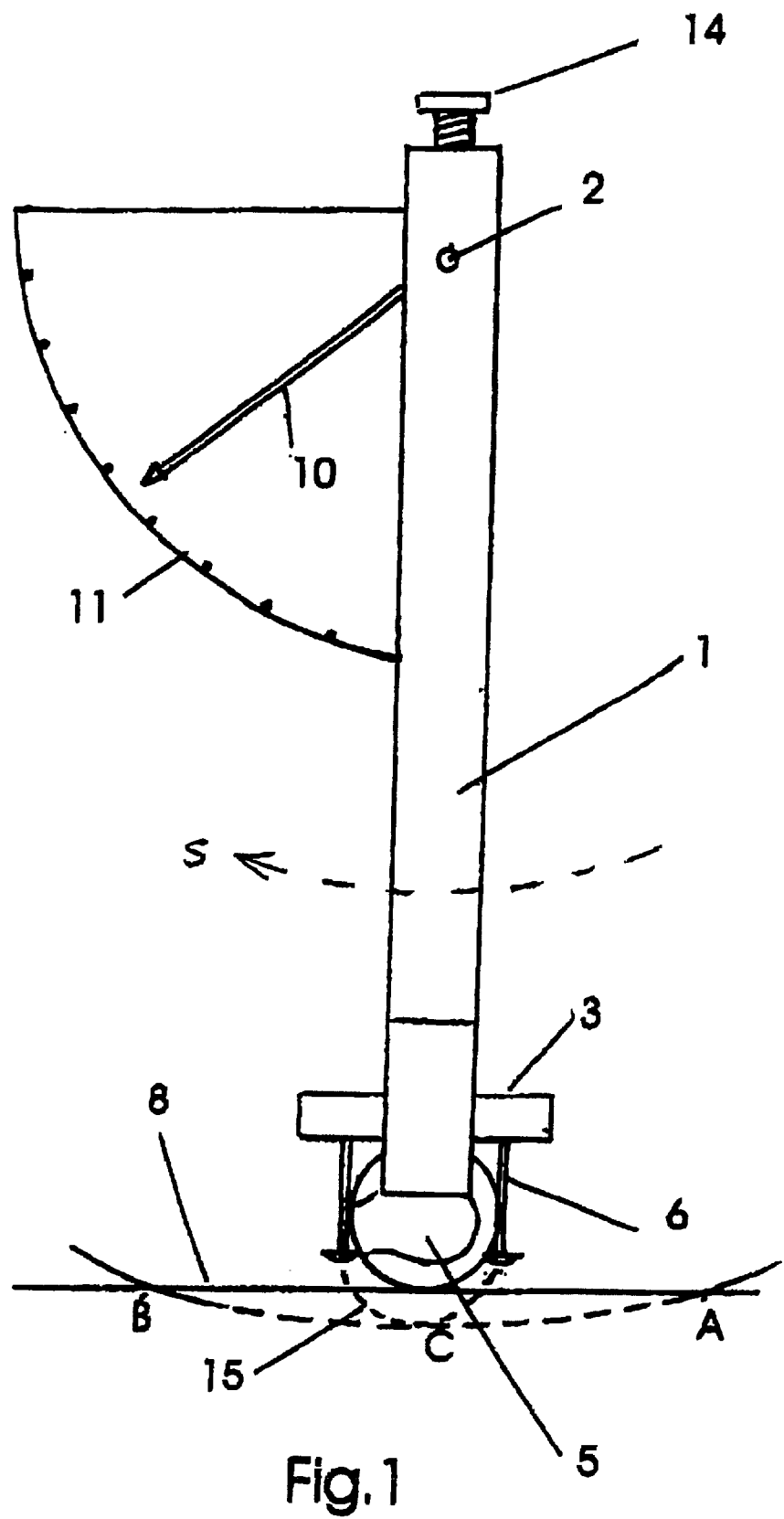
FIG. 1 is a side elevation of a device embodying the invention.
Figure 2:
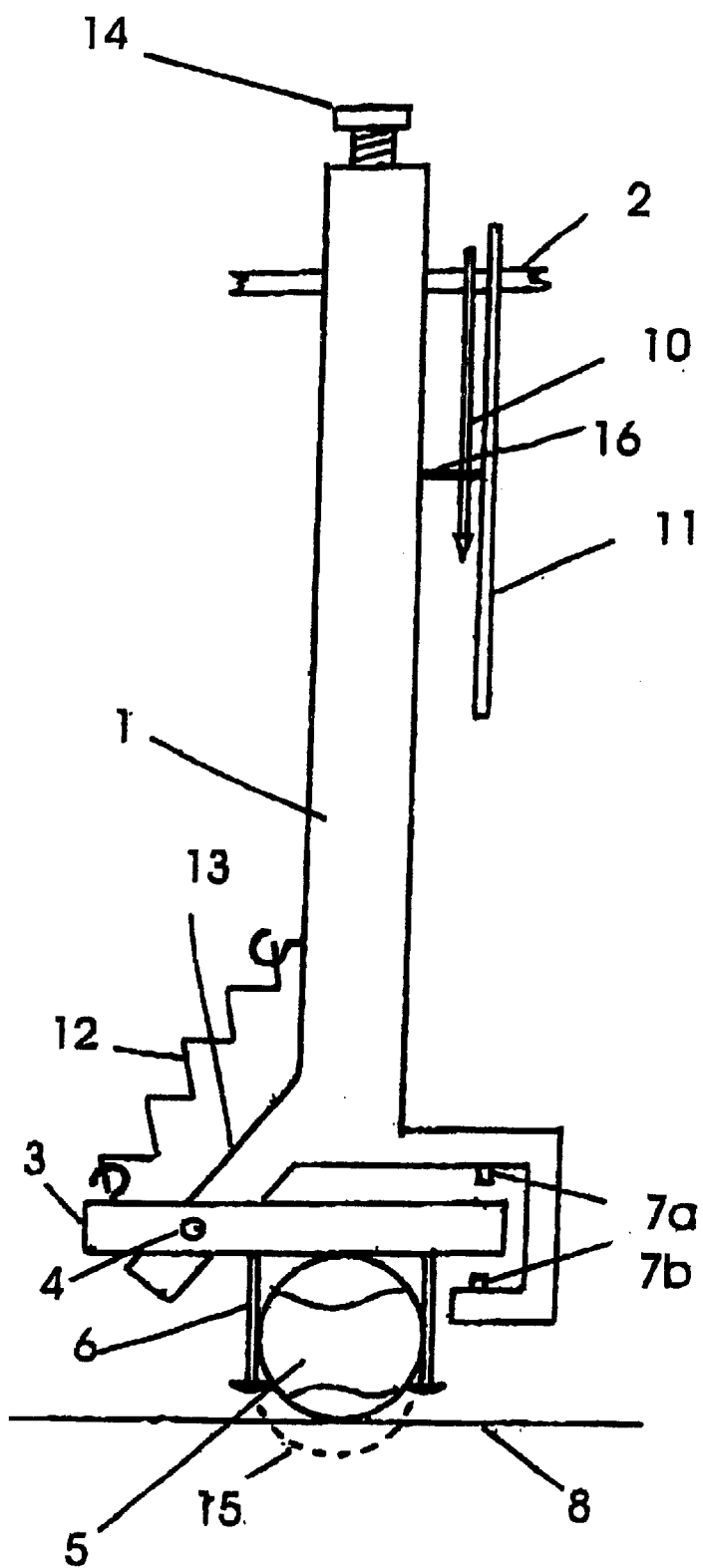
FIG. 2 is a rear elevation of the same device.
Figure 3:
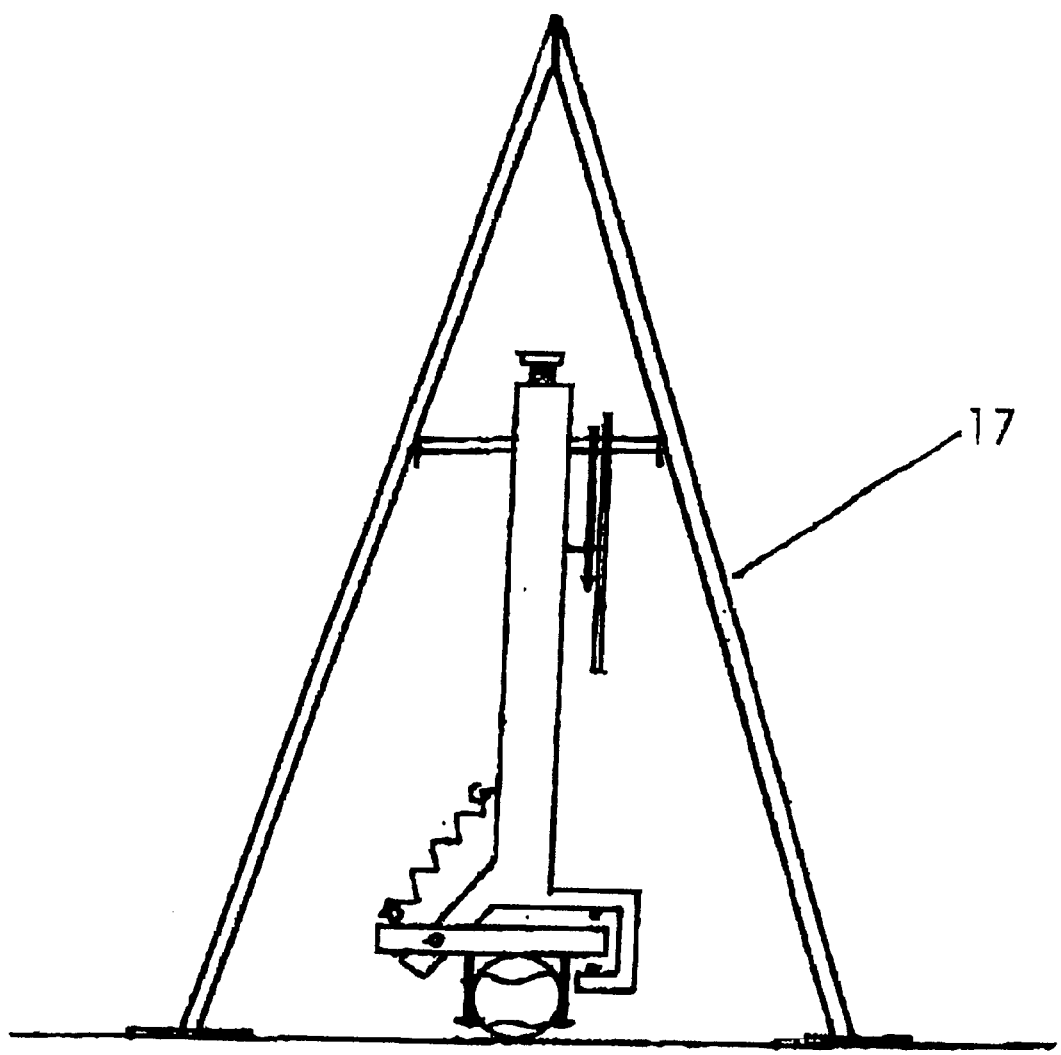
FIG. 3 is the device of FIG. 2 supported on a tripod framework.

A preferred embodiment of the device is shown in FIGS. 1 and 2. The pendulum 1 is pivoted at 2 in a tripod framework 17 such that the pivot can be moved by a screw device 14 in a vertical direction and subsequently locked in position so that the height of this pivot can be set at different heights above the test surface 8.

Adjustment of the height of the pivot is desirable in order to allow for:

(i) surfaces which distort under the weight of the ball/shoe when setting-up for a test (see (3) below);

(ii) balls which distort under the same weight, such as soft tennis balls; and (iii) testing of sample pieces of the test surface, which may be placed between the legs of the tripod framework and thus raised above the surface on which the framework stands. For example, a piece of synthetic carpet material such as a carpet tile could be tested in this way.

The ball 5 is shown in a holder 6 which is attached to a shoe 3 pivoted at 4 to a projection 13 extending laterally from the end of the pendulum. The holder is designed to hold the ball firmly so that it cannot rotate on striking the surface.

The movement of the shoe is restricted by stops 7a and 7b, and a load is applied to the shoe so as to hold the ball against the surface 8 by tension spring 12. The contact path AB of a point on the ball furthest from the pendulum's pivot is shown where it is constrained to contact and move along the test surface rather than through arc ACB (which it would follow if the surface was not present—the ball position shown dotted at 15) before and after which the lower stop 7b prevents contact as the pendulum swings through its arc. The height to which the pendulum swings after the ball has contacted the surface is measured on scale 11 by slave pointer 10 which is controlled by peg 16 on the pendulum 1.

The pendulum may be made of wood, metal or fiber-reinforced plastic. In one specific example, the pendulum is set up so that its pivot 2 is 0.98 m above the test surface, with a distance from its center of gravity to the pivot of 0.54 m, and a moment of inertia about the pivot of 0.277 kgm$^2$.

In carrying out a test the following sequence of operations is followed.

(1) The tension spring 12 is removed and the ball 5 is fitted into the holder making sure that it is firmly seated.

(2) With the pendulum vertical (at rest), its pivot 2 is moved up with respect to the test surface 8 by operating screw 14 until the ball is not touching the surface because its degree of pivoting about pivot 4 is restricted by lower stop 7b.

(3) Keeping the pendulum vertical, the pivot 2 is then moved downwards with respect to the test surface until the ball touches the surface and this downward movement is continued until the gap between the shoe and the upper stop 7a reaches a pre-determined setting as judged by a feeler gauge. The pivot of the pendulum is then locked in position so fixing its height above the test surface taking account of the weight of the shoe/holder/ball acting about the shoe's pivot. This is particularly important where deformable surfaces are to be tested.

(4) The tension spring 12 is then replaced. This acts about the shoe's pivot so forcing the shoe to contact the lower stop 7b when the pendulum is raised from the vertical position. In the above specific example, the permitted movement of the shoe from the set-up position in the direction along the radius from pivot 2, until limited by stop 7b, is pre-set to between 0.5 and 2.0 cm (0.2 to 0.8 inches) depending on the length of contact path required.

(5) The pendulum is then raised by an operator (tester) by rotating it (anticlockwise in FIG. 1) until its axis is horizontal and the slave pointer (10) is set to zero.

(6) The pendulum is allowed to fall so as to describe a vertical arc in the direction indicated by S in FIG. 1. During the lower (middle) portion of this arc, the ball contacts the surface over a distance AB which is pre-determined by the setting of the lower stop 7b. At this time, the ball is held against the surface by the tension of spring 12 (which also prevents any unwanted rebound).

(7) The pendulum carries the slave pointer to indicate its maximum angle of swing after the ball contacts the surface and the pendulum is restrained (e.g. caught by the operator) before it falls back towards the surface.

(8) The scale reading is taken and the loss in energy of the pendulum assessed. This can be related to the friction existing between the ball and surface as explained below.

The initial setting-up procedure referred to in paragraphs (1) to (4) is preferable so that surfaces of different texture and deformability may be evaluated and also balls of different diameter can be used. In this way the effective length of the pendulum is set under the action of the moment of weight of the ball-holder/shoe assembly only bearing onto the surface so that the combined deflection of the ball/surface is taken into account initially and the pendulum's pivot height set accordingly. This is particularly important when fibrous surfaces (eg grass) are being evaluated.

In considering the mechanics of the system, it might be thought that the fact that the ball/holder moves radially (under control of the stops) with respect to the pendulum's pivot as it moves to and through the ball surface contact area would negate the validity of the use of change of energy to measure the force of friction operating. On reflection it will be seen that this change in radius occurs both on entering and leaving the contact area and so the two effects cancel out and do not affect the outcome.

Measuring the extent of the pendulum swing following contact of the ball with the surface enables the coefficient of friction between the two to be calculated.

The theoretical basis for this will now be explained. In the following analysis:

P=the energy input by the pendulum falling from the horizontal.

E=% of input energy remaining after ball surface contact.

E*=% of input energy remaining corrected for system losses.

e=the corrected energy loss as % of input energy.

d=contact path length.

R=the vertical force (or reaction) between ball and surface.

F=force of friction.

$\mu$=coefficient of friction.

It is assumed that during ball/surface contact, F and R are constant.

The energy loss in the pendulum system due to bearing friction and air resistance is measured by allowing the pendulum to fall from the horizontal so that the ball does not contact the surface and the % of energy remaining measured from the scale. This was measured at 92% in experiments conducted so that:

$$E^* = 100.E/92$$

Therefore corrected % energy loss e=100−E* which can be calculated for each scale reading.

$$\text{Now actual energy loss} = e \cdot P$$
$$= \text{Work Done against Friction}$$
$$= F \cdot d$$
$$\text{But } F = \mu \cdot R$$

-continued
$$\text{Therefore } e \cdot P/d = \mu \cdot R$$
$$\text{so } \mu = e \cdot P/R \cdot d$$

If values of R and d are varied for a known P and measured e, then the coefficient of friction $\mu$ can be found.

Values of P,R and d used in trials were as follows:

P=0.794 J (Joule);

R=(a) 1.94 Kg. (4.25 lb) and (b) 2.30 Kg (5 lb);

d=(i) 0.246 m (9.7 in.) and (ii) 0.338 m (13.8 in)

Typical data is given below for tests using a tennis ball on three different surfaces, using two different combinations (a) and (b) of the load R on the ball, and two values (i) and (ii) of contact path length d. The length of the contact path is adjusted by setting the position of stop 7b as mentioned above, the values (i) and (ii) below corresponding to permitted radial movements set by stop 7b of 0.75 and 1.71 cm respectively (0.3 and 0.67 in respectively).

| Surface | Load R | | (i) .246 m | | | | (ii) .338 m | | | |
|---|---|---|---|---|---|---|---|---|---|---|
| | | | E | E* | e | $\mu$ | E | E* | e | $\mu$ |
| Wood | (a) | 1.94 Kg | 72 | 78 | 22 | .37 | | | | |
| | (b) | 2.30 kg | | | | | 60 | 65 | 35 | .36 |
| Plastic | (a) | 1.94 kg | 60 | 65 | 35 | .58 | | | | |
| Carpet | (a) | 2.30 kg | | | | | 35 | 38 | 62 | .63 |
| Concrete | (a) | 1.94 kg | 64 | 70 | 30 | .50 | | | | |
| | (b) | 2.30 kg | | | | | 49 | 53 | 47 | .48 |

(One kg (kilogram) is approximately 2.2 lbs).

It should be noted that, in the embodiments described above, the ball is fixed so that it does not rotate on contact with the surface and so a sliding rather than a rolling motion is produced which is considered to be more significant in terms of the ball/surface interaction.

As an alternative, however, the holder could be adapted to permit rotation of the ball within the holder. For example, a roller or ball bearing could be mounted within the upper part of an enlarged holder, having an exposed rolling surface bearing against the test ball. Alternatively, a fixed surface could bear against the test ball. In either case, the surface could be arranged to permit either free or restrained (braked) rotation as desired.

The described embodiment employs a pointer 10 and scale 11 in order to display the extent of the pendulum swing. However, this is not essential and particularly in cases where a small-sized device is needed, the scale and pointer may be replaced by an electrical or electronic device (rotary position sensor) having a dial or readout for displaying the angle obtained. This would normally be located on or linked to the pivot 2 in order to detect rotation of the pendulum about that pivot.

What is claimed is:

1. A device for determining the friction between a games ball and a playing surface, comprising:
    a rigid pendulum mounted by a pivot at a first end thereof to a frame placed on the surface, allowing the pendulum to describe an arc by swinging in a first plane vertical to the surface;
    a holder for holding a ball at or adjacent a second end of the pendulum;
    means for adjusting the position of the pivot relative to the surface, and/or for adjusting the position of the ball relative to the pivot, to ensure contact of the ball with the surface over a desired length of a lower portion of the arc; and means for measuring the extent of the arc described by the pendulum following contact of the ball with the surface, so as to allow determination of the friction between the two;

wherein the holder is attached to the pendulum by a rotatable shoe arranged such that:

the shoe is able to rotate relative to the pendulum in a second plane perpendicular to the first plane and which passes through the longitudinal axis of the pendulum such that the centre of the ball can move in a controlled manner in an approximately radial direction with respect to the pendulum pivot; and at a point where the pendulum is vertical, the centre of the ball lies on a vertical line passing through that pivot.

2. A device according to claim 1, wherein the shoe is free to rotate in said second plane within a range of movement defined by adjustable stops provided on the pendulum, thereby defining the extent of movement of the ball holder in said radial direction in order to control the length of contact between the ball and the surface.

3. A device according to claim 1, wherein the shoe is pivoted from a lateral projection of the pendulum, allowing the holder and ball to be disposed underneath the end of the pendulum such that rotation of the shoe in said second plane moves the ball substantially along the axis of the pendulum.

4. A device according to claim 1, wherein a load is applied to the shoe by means of interchangable springs so that the force applied by the ball to the surface in a direction vertical to the surface may be varied.

5. A device according to claim 4, wherein each of said springs is a tension spring extended between a point on the shoe and a point part-way along the pendulum.

6. A device according to claim 1, wherein the means for holding the ball is adapted to hold the ball in a firmly fixed position for determination of sliding friction.

7. A device according to claim 1, wherein the means for holding the ball is adapted to hold the ball in such a way as to permit either free or restrained rotation of the ball within the holder, to allow determination of rolling friction.

8. A device according to claim 1, wherein the adjusting means comprises a screw to which the pendulum pivot is attached, and which is screw-mounted in the frame and capable of being locked in position.

9. A device according to claim 1, wherein the measuring means comprises a scale placed parallel to the plane of the pendulum arc, and a slave pointer which is rotatable in said first plane about the pendulum pivot to follow the pendulum, and wherein the slave pointer is arranged to hold its position when the pendulum arc reaches its maximum extent following contact of the ball with the surface.

10. A device according to claim 1, wherein the holding means is adapted to hold a tennis ball.

11. A method of determining the frictional force between a games ball and a playing surface, comprising the steps of:

retaining a rigid pendulum at one end to a pivot fixed above the surface, allowing the pendulum to swing in a first plane vertical to the surface;

mounting a ball at or adjacent the other end of the pendulum via a shoe which is rotatably mounted to the pendulum in such a way as to rotate relative to the pendulum in a second plane perpendicular to the first plane and which passes through the longitudinal axis of the pendulum;

adjusting the height of the pivot above the surface, and/or adjusting the position of the ball relative to the pivot, in order to ensure contact of the ball with the surface over a desired length of the lower part of the pendulum swing;

measuring the extent of the pendulum swing following contact of the ball with the surface; and determining the frictional force between the ball and the surface based on the measured extent of the pendulum swing.

12. A method according to claim 11, wherein:

in said mounting step, the ball is inserted in a holder attached to a rigid pendulum via the shoe;

in said adjusting step:

(i) the height of the pendulum pivot above the test surface is adjusted so that the moment of weight of the shoe/holder/ball only is applied to the surface through the ball and a fixed distance is set between the shoe and a fixed upper stop;

(ii) a spring is then fitted to apply a load to the shoe such that it is pressed down against a lower stop when the pendulum is raised from the vertical and such that when the pendulum is vertical the spring becomes extended so that an additional force is applied to the surface through the ball; and (iii) the lower stop is adjusted to give a ball/surface contact path of known length as the pendulum describes its lower arc; and in said measuring step, the pendulum is raised to a pre-determined height and released so that the ball descends towards, then contacts and slides along the surface as the pendulum describes its arc, and the maximum angle of the pendulum's swing after ball/surface contact is measured by the slave pointer.

* * * * *